(12) United States Patent
Fingal et al.

(10) Patent No.: US 8,637,728 B2
(45) Date of Patent: Jan. 28, 2014

(54) NON-WOVEN MATERIAL FOR USE AS A BODY FACING SHEET IN AN ABSORBENT ARTICLE

(75) Inventors: Lars Fingal, Göteborg (SE); Jeanette Hellström, Göteborg (SE)

(73) Assignee: SCA Hygiene Products AB, Gothenburg (SE)

( * ) Notice: Subject to any disclaimer, the term of this patent is extended or adjusted under 35 U.S.C. 154(b) by 601 days.

(21) Appl. No.: 12/599,435

(22) PCT Filed: May 30, 2007

(86) PCT No.: PCT/SE2007/050372
§ 371 (c)(1),
(2), (4) Date: Nov. 9, 2009

(87) PCT Pub. No.: WO2008/147264
PCT Pub. Date: Dec. 4, 2008

(65) Prior Publication Data
US 2010/0249741 A1    Sep. 30, 2010

(51) Int. Cl.
*A61F 13/15* (2006.01)
*A61F 13/20* (2006.01)

(52) U.S. Cl.
USPC .......................................... 604/367; 604/378

(58) Field of Classification Search
USPC ........................................ 604/367, 370, 378
See application file for complete search history.

(56) References Cited

U.S. PATENT DOCUMENTS

| | | | |
|---|---|---|---|
| 4,041,203 A | 8/1977 | Brock et al. | |
| 4,443,297 A | 4/1984 | Cheshire et al. | |
| 5,114,787 A | 5/1992 | Chaplin et al. | |
| 5,820,615 A | 10/1998 | Koczab | |
| 5,951,535 A | 9/1999 | Fujiwara et al. | |
| 7,432,219 B2 * | 10/2008 | Strandqvist et al. | 442/408 |
| 2002/0090875 A1 | 7/2002 | Lasko et al. | |
| 2004/0010894 A1 * | 1/2004 | Goldwasser et al. | 28/104 |
| 2006/0012072 A1 * | 1/2006 | Hagewood et al. | 264/176.1 |
| 2006/0121811 A1 | 6/2006 | Mangold et al. | |

FOREIGN PATENT DOCUMENTS

| | | |
|---|---|---|
| CA | 841938 | 5/1970 |
| EP | 0938601 | 12/2001 |
| GB | 1329409 | 9/1973 |
| GB | 2 278 371 A | 11/1994 |
| JP | 06-136654 | 5/1994 |
| JP | 2001-046433 | 2/2001 |
| JP | 2006-517263 | 7/2006 |
| JP | 2006-241644 | 9/2006 |
| WO | 91/14414 | 10/1991 |
| WO | 96/02701 | 2/1996 |
| WO | 96/41045 | 12/1996 |
| WO | 02/44456 | 6/2002 |
| WO | 02/49567 | 6/2002 |
| WO | 03/017902 | 3/2003 |
| WO | WO 2004/063451 A1 | 7/2004 |

* cited by examiner

*Primary Examiner* — Michele M Kidwell
(74) *Attorney, Agent, or Firm* — Drinker Biddle & Reath LLP

(57) ABSTRACT

A nonwoven material including at least two layers integrated into each other, for use as a body facing sheet in an absorbent article. The first layer includes spunlaid filaments and the second layer includes staple fibers. The staple fibers have a thickness ≤1.5 dtex, and the filaments have a thickness ≥2.5 dtex. Further, an absorbent article, such as a sanitary napkin, panty liner, incontinence protector or diaper can include the nonwoven material as a body facing sheet.

13 Claims, 4 Drawing Sheets

NON-WOVEN MATERIAL FOR USE AS A BODY FACING SHEET IN AN ABSORBENT ARTICLE

CROSS-REFERENCE TO PRIOR APPLICATION

This application is a §371 National Stage Application of PCT International Application No. PCT/SE2007/050372 filed May 30, 2007.

FIELD OF THE INVENTION

The present disclosure relates to a nonwoven material for use in an absorbent article as a body facing sheet and an absorbent article comprising the nonwoven material.

BACKGROUND

Absorbent articles often comprise a liquid permeable top sheet, a liquid impermeable bottom sheet and optionally an absorbent airlaid layer arranged between the top sheet and the bottom sheet. The top sheet might be made of two layers of spunbond filaments having a thickness of 3 dtex. A very good liquid inlet function is achieved with such a material. The top sheet of spunbond/spunbond filaments is however not comfortable for the user, since the filaments are coarse and the sheet is not soft. Thus, coarse filaments give a good inlet property but the softness is not satisfactory. Finer filaments will make the layer softer, but such a layer will have a poorer inlet function. A soft feeling may also be achieved using filaments such as cotton, viscose, lyocell, having a high softness and textile comfort. However, these filaments bind liquid and prevent the liquid from passing through the top sheet to the absorbent layer. Such a surface will give a wet feeling against the user during and it will be uncomfortable for the user.

Further, top sheets in the form of nonwoven materials comprising a layer of continuous filaments and a layer comprising short fibres have also been used. Such a top sheet is disclosed in for example U.S. Pat. No. 5,951,535. The layer including the short fibres comprises hot-melt-adhesive composite short fibres and they are hot-melt adhered together. The short fibres will be crimped and a bulky nonwoven material will be obtained. The hot melt adhesion will result in thermobonding, which is disadvantageous for the inlet function and the comfort during use.

WO 02/44456 A2 relates to a nonwoven material comprising a nonwoven web on which micro-fine fibres of great length are deposited as an aqueous slurry. The nonwoven web comprises fibres which are meltblown, spunbond, coformed, bonded and carded or airlaid. The microfine fibres could be used for adjustment of the rate of fluid movement through a personal care product. Such a layer becomes very dense.

It is desired to improve top sheet materials in absorbent articles and to solve the problems above.

SUMMARY

The present disclosure relates to a nonwoven material comprising at least two layers integrated into each other, for use as a body facing sheet in an absorbent article, wherein the first layer comprises spunlaid filaments and the second layer comprises staple fibres, wherein the staple fibres have a thickness ≤1.5 dtex and the filaments have a thickness ≥2.5 dtex. The layer comprising fibres having a thickness ≤1.5 dtex give a soft feeling and the layer comprising filaments having a thickness ≥2.5 dtex give a very good property of letting liquid through the layer. The combination of the layers and their respective properties will give a nonwoven material that works very well as a body facing sheet in an absorbent article.

Further, the disclosure concerns an absorbent article, such as a sanitary napkin, panty liner, incontinence protector or diaper, comprising the nonwoven material as a body facing sheet.

DEFINITIONS

As used herein, "filaments" refers to fibres that in proportion to their diameter are very long, in principle endless. They can be produced by extruding a molten thermoplastic polymer through fine nozzles, followed by the polymer will be cooled and drawn, for example by the action of an air flow blown at and along the polymer streams, and solidified into strands that can be treated by drawing, stretching or crimping. Chemicals for additional functions can be added to the surface.

Filaments can also be regenerated fibres produced by chemical reaction of a solution of fibre-forming reactants entering a reagent medium, for example by spinning of regenerated cellulose fibres from a cellulose xanthate solution into sulphuric acid. Examples of regenerated cellulose fibres are viscose and lyocell fibres.

The term "staple fibres" is used herein. The staple fibres can be produced from, the same substances and by the same processes as the filaments discussed above. They may either be synthetic fibres or regenerated cellulose fibres, such as viscose or lyocell fibres. Further, silk fibres can also be used. The cutting of the fibre bundles is normally done to result in a single cut length.

By "body fading sheet" is meant a sheet which is the sheet closest to the body of the user. A body facing sheet could for example be a top sheet in an absorbent article. It could also be the sheet closest to the body of the user of the belt members, the side panels and the area in the waist part of an article.

DETAILED DESCRIPTION OF PREFERRED EMBODIMENTS

Figure 1:
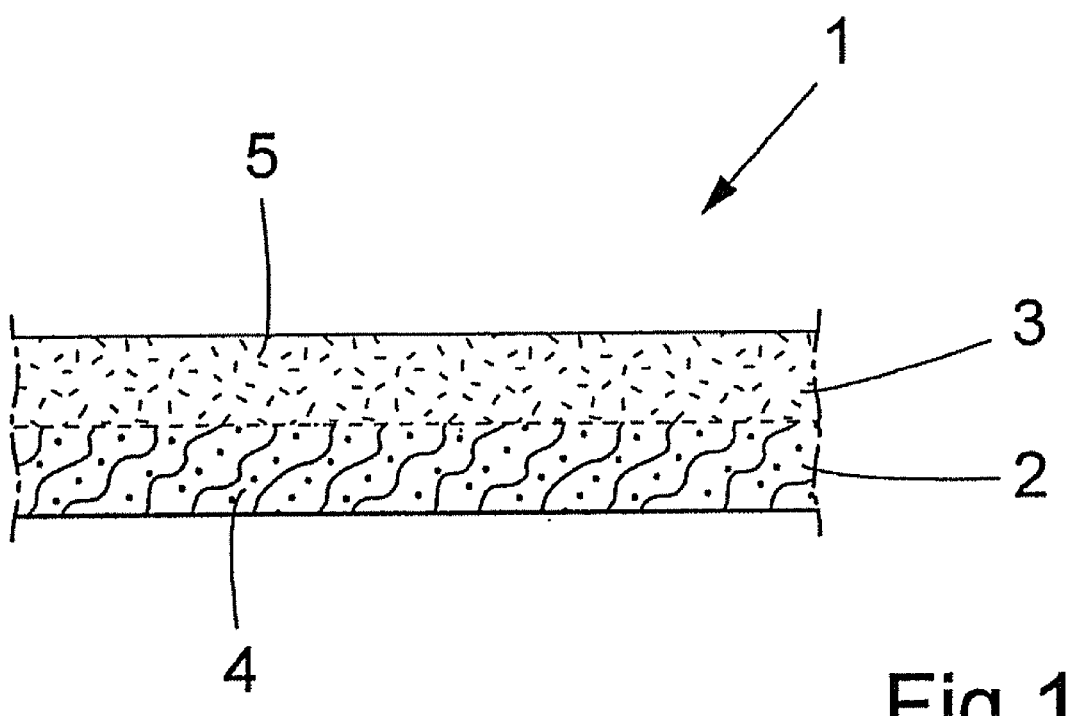
FIG. 1 shows a cross-section of a nonwoven material according to an embodiment of the present invention.

An embodiment of the invention includes a nonwoven material, shown in FIG. 1, comprising at least two layers 2, 3 integrated into each other, for use as a body facing sheet in an absorbent article, wherein the first layer 2, comprises spunlaid filaments 4 and the second layer 3 comprises staple fibres 5, wherein the staple fibres 5 have a thickness ≤1.5 dtex and the filaments 4 have a thickness ≥2.5 dtex. The nonwoven material may be used in an absorbent article, and in such a case the second layer 3 comprising the staple fibres 5 is directed against the user during use. This part of the sheet comprising fibres as thin as ≤1.5 dtex is soft and feels pleasant for the user, due to the thin staple fibres 5. At the same time, the first layer 2 comprising the filaments 4 which are relatively coarser than the staple fibres 5, have a good liquid inlet property. The body facing sheet 1 can have a soft surface layer, i.e. the second layer 3, combined with the first layer 2 comprising the filaments. The filament layer 2 may work as a transfer layer, through which liquid, such as urine, menstrual blood and sweat, will be transferred quickly to a lower layer in the absorbent article. The first layer 2 comprising coarse filaments 4 can have pores that are relatively large so the liquid can pass through the layer quickly. The body facing sheet may be a top sheet. The properties of soft and pleasant feeling in the second layer 2 against a user and the liquid inlet properties in the first layer 3 are properties that can be an advantage in a top sheet in an absorbent article. Further examples of a body facing sheet will be given below.

The nonwoven layer is produced by a method which will be disclosed in more detail later in the description. Shortly, the first layer 2 can be spunlaid on a forming member, which means that the filaments are spun and solidified before they reach the forming member. The staple fibres can be then air-laid, or wet-laid onto the first layer. If the staple fibres are wet-laid, they may be foam-formed on top of the first layer. The binding between the layers can be made by hydroentangling. Thus, no thermobonding is used, which is advantageous since thermobonding creates liquid barriers created by melted fibres in the top sheet. The layers are hydroentangled which can lead to that the fibres and filaments going into the other respective layer so that the layers are thereby integrated into each other. This means that no clear boundary is found between the two layers. The hydroentangling bonding can be an advantage for the nonwoven material, since, for example, this avoids barriers for liquids in the material. If thermobonding would be used to bind the layers together, the layers would need to be dried before the thermobonding step. Such a drying step requires extra energy.

The nonwoven material may comprise staple fibres in the second layer that have a thickness ≤0.7 dtex. With this thickness the feeling will be even softer against the user. The thinner the fibres are the softer feeling will be obtained. A nonwoven material according to the present invention may also comprise staple fibres having a thickness ≤0.5 dtex. This will give a body facing sheet or a top sheet with a pleasant feeling against the user, while the liquid inlet in the top sheet will be very good.

The staple fibres in the second layer may have a length of 6 to 40 mm. The staple fibres may be wetlaid or airlaid onto the first layer comprising filaments. However, they may also be carded separately, before the carded layer is laid down onto the filament layer. When the staple fibres are carded, they have a length of about 20-40 mm, since the fibres shall hook into each other. Shorter fibres are difficult to card. When the staple fibres are wetlaid or airlaid, they may be shorter, i.e. 6 to 20 mm. Wetlaid or airlaid staple fibres may be laid down in small amounts, which may be an advantage for obtaining very thin layers of the staple fibres.

The filaments can have a thickness ≥3 dtex. A layer made of coarse fibres will have good liquid inlet properties.

Many different materials are possible to use for the nonwoven material. The filaments and fibres may be chosen from man-made fibres. Man-made filaments and fibres are divided in filaments and fibres made from natural polymers, synthetic polymers and synthetic polymers from renewable resources. All these kind of polymers can be used in the filaments and fibres used in the nonwoven material. Further, silk fibres which belong to natural fibres may be used as staple fibres.

Thus, the filaments can be chosen from synthetic fibres and synthetic fibres from renewable resources. Synthetic filaments may be polyolefin filaments, such as polyethylene and polypropylene fibres, polyamide filaments, polyester filaments, and polyacrylic filaments. Synthetic filaments from renewable recourses may be polylactide filaments. Copolymers of the polymers used for the production of the filaments mentioned above may, also be used for producing filaments for the nonwoven material.

The staple fibres can also be chosen from natural fibres, synthetic fibres and synthetic fibres from renewable resources. Synthetic fibres may be polyolefine fibres, such as polyethylene and polypropylene fibres, polyamide fibres, polyester fibres, and polyacrylic fibres. Synthetic fibres from renewable recourses may be polylactide fibres. Copolymers of the polymers used for the production of the fibres mentioned above may also be used for producing fibres for the nonwoven material. Fibres may also be produced from natural polymers. Thus, viscose fibres and lyocell fibres may be used in the nonwoven material. The staple fibres may also be silk fibres, which are natural fibres. All the fibres mentioned above should give a soft surface.

The fibres and filaments which may be used are chosen for several reasons. At least one reason is the permeability of liquid. The staple fibres should be soft and should neither absorb liquid in any great extent.

The nonwoven material may have a surface weight of 20-50 g/m². An embodiment of the present invention in includes a nonwoven material wherein the staple fibres constitute 10-40% by weight of the material, calculated on the total weight of the nonwoven material, and the filaments constitute 60-90% by weight of the material, calculated on the total weight of the nonwoven material. Staple fibres are expensive and the amount is desired to be quite low. Further, liquid is attracted to the smaller pores in the second layer and it is desired that this layer is quite thin for avoiding liquid to stay in the second layer comprising staple fibres. 10% by weight is about enough to be able to make a second layer 3 which will cover the first layer 2. More than 40% by weight staple fibres will make the layer too dense which will prevent liquid from passing through the second layer. 60% by weight filaments will give a layer which has a good liquid inlet and the liquid will pass the layer quite fast. More than 90% by weight will not be comfortable for the user. Further, the first layer comprising filaments will have larger pores than the second layer comprising staple fibres. The first layer may work as a transfer layer between the second layer and a lower layer, such as an absorption layer. The pore size in the first layer will increase successively from the interface between the two layers to the bottom of the first layer. This is also due to that the layers are hydroentangled together.

The body facing sheet may be a top sheet, a sheet used as a waist part, a side panel or a belt member. Hence, all description and all definitions above also refer to these embodiments of the present invention. A belt member may be attached to a rear portion, alternatively to a front portion of a diaper and are intended to be fastened together around the waist of a wearer by fastening means. Such belt members are disclosed in for example WO 03/017902 A1. A side panel in a diaper is a part in the front or rear part, on which for example a belt member is attached to. Side panels are disclosed in for example WO 02/49567. The waist part is the part, when the article is in use, which is situated in the waist area of a wearer. Waist parts are present in diapers or pull-on pants.

The body facing sheet used as a top sheet, in a waist part, a side panel or a belt member will, as defined, be the sheet closest to the body of the user. The soft second layer will be faced against the body of the user, since this is the soft and smooth layer. Since the second layer is directed against the body of the user, the first layer is directed away from the body of the user. A belt member, side panel, or a waist part may comprise only the nonwoven material. If this is the case, the first layer will be detached on the outer surface of an absorbent article and available from the outer surface. By "outer surface" is then meant the surface directed from the body of the user when the article is in use on the body of the user. In such a case, the body facing sheet, if placed in the waist part or in the belt members, could be used as a loop material for attaching a hook material for attachment means in an absorbent article. It is the first layer comprising spunlaid filaments that will be used for attachment of hook material. Since the body facing sheet is soft and smooth, besides having good liquid inlet properties, it is also suitable for use in body facing sheets which do not cover the absorbent core, which is the case with the waist part, the belt members or the side panels.

Another embodiment includes an absorbent article, such as a sanitary napkin, panty liner incontinence protector or a diaper, comprising a nonwoven material as disclosed above. The nonwoven material is used as a body facing sheet. The body facing sheet may be a top sheet, a sheet in a belt member, side panel or a waist part as disclosed above. Further, the nonwoven material could be used as loop material in an absorbent article. In the following, the body facing sheet will be described as a top sheet, but the definitions and characteristics given will also cover the other embodiments of a body facing sheet.

Figure 2:
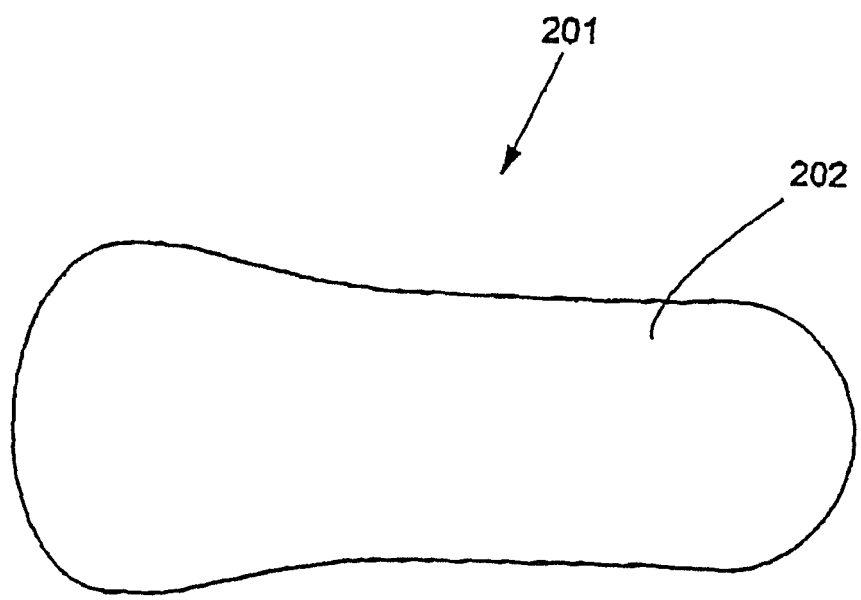
FIG. 2 shows an embodiment of a sanitary napkin according to an embodiment of the present invention.

The absorbent article may comprise a nonwoven material as a top sheet and further a bottom sheet and possibly interjacent layers as described below. An embodiment in the form of a sanitary towel 201 is illustrated in FIG. 2, wherein the sanitary napkin comprises a nonwoven material as the top sheet 202. The second layer is directed against the body of the user during use. Also included is a bottom sheet, which is not shown here, and possibly interjacent layers as described below. The nonwoven material comprises at least two layers 2, 3, wherein the first layer 2 comprises spunlaid filaments 4 and the second layer 3 comprises wetlaid or airlaid staple fibres 5, wherein the staple fibres 5 have a thickness ≤1.5 dtex and the filaments 4 have a thickness ≥2.5 dtex.

Figure 3:
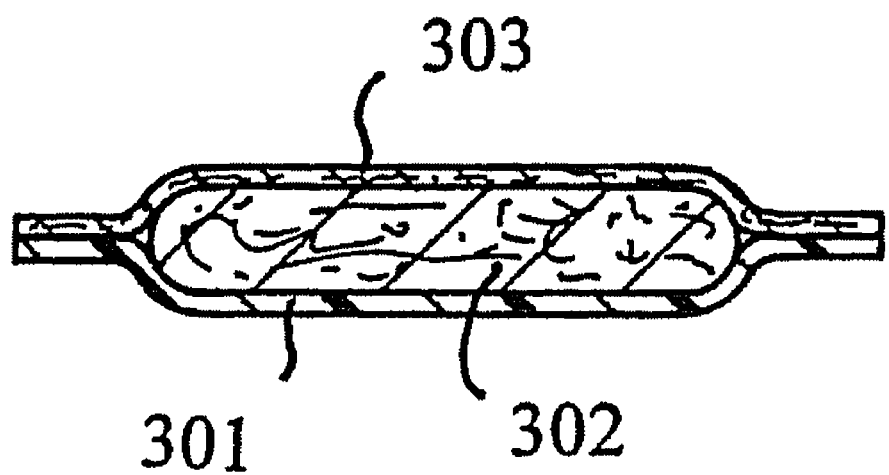
FIG. 3 shows a cross-section of the sanitary napkin in FIG. 2.

FIG. 3 discloses a cross-section of the absorbent article in FIG. 2. The bottom sheet 301 may include a flexible film, for example a plastic film. Examples of plastic materials in the film are polyethylene (PE), polypropylene (PP), polyester or some other suitable material, such as a hydrophobic nonwoven layer or a laminate of a thin film and a nonwoven material. These types of material are often used in order to achieve soft and textile-like surface on the bottom sheet 301. The bottom sheet 301 can be breathable, so that it permits vapour to pass through while also preventing penetration by liquid. The breathable materials can include porous polymer films, nonwoven laminates produced from spunbonded and meltblown layers, and laminates produced from porous polymer films and nonwoven materials.

The bottom sheet can have an adhesive attachment in the form of beads of adhesive, for example, on the side of the bottom sheet that faces away from the upper layer, to enable them to be secured in panties, underpants or knickers. A release material may be applied on top of the adhesive in order to protect the adhesive when the product is not in use.

The absorbent product can also comprise an absorbent core 302 or structure, between the top sheet 303 and the bottom sheet 301. The absorbent core 302 can be constructed from one or more layers of cellulose fibres, for example cellulose fluff pulp, airlaid, fluff pulp, dry defibred or compressed pulp. Other materials that can be used include, for example, absorbent nonwoven material, foam material, synthetic fibre material or peat. Apart from cellulose fibres or other absorbent materials, the absorbent core can also comprise superabsorbent materials, so-called SAP (superabsorbent polymers), which are materials in the form of fibres, particles, granules, films or the like. Superabsorbent polymers are inorganic or organic materials that are capable of swelling in water and are insoluble in water, which exhibit the capacity to absorb at least 20 times their own weight of an aqueous solution containing 0.9% by weight of sodium chloride.

Organic materials that are suitable for use as a superabsorbent material can include natural materials such as polysaccharides, polypeptides and the like, as well as synthetic materials such as synthetic hydrogel polymers. Such hydrogel polymers can include, for example, alkaline metal salts of polyacrylic acids, polyacrylamides, polyvinyl alcohol, polyacrylates, polyacrylamides, polyvinyl pyridines and the like. Other suitable polymers include hydrolysed acrylonitrilegrafted starch, acrylic acid-grafted starch, and isobutylene maleic acid anhydride co-polymers and mixtures thereof. The hydrogel polymers are preferably readily cross-linked to ensure that the material remains essentially insoluble in water. The preferred superabsorbent materials are also surface cross-linked so that the external surface or the shell of the superabsorbent particle, fibre, sphere, etc., has a higher cross-linking density than the inner part of the superabsorbent. The proportion of superabsorbents in an absorbent core can be between 10 and 90% by weight, or preferably between 30 and 70% by weight.

The absorbent core can comprise layers of different materials with different characteristics with regard to their ability to receive liquid, liquid distribution capacity and storage capacity. The absorbent core is more often than not extended in the longitudinal direction and can, for example, be rectangular, T-shaped or hourglass-shaped. An hourglass shaped core is wider in the front and rear parts than in the crotch part, in order to provide effective absorption, at the same time as the design makes it easier for the product to be formed close to and around the wearer, thereby providing a better fit around the legs.

The absorbent product can also include a transport layer between the top sheet and the absorbent core. The transport layer is a porous, flexible material and can comprise one or more of the following: airlaid, wadding, tissue, carded fibre web, superabsorbent particles or superabsorbent fibres. A transport layer has a high instantaneous capacity to receive liquid and is able to store liquid temporarily before it is absorbed by the subjacent absorbent core. The transport layer can cover the whole or parts of the absorbent core.

The top sheet, the bottom sheet and any interjacent materials can be sealed at the edges of the product, which can be effected by thermal sealing, for example, or by some other conventional means.

The absorbent product can also comprise wings on its sides. It can also comprise elastic in order to provide better contact with the body when, the product is being worn, and also to, reduce leakage.

Figure 4:
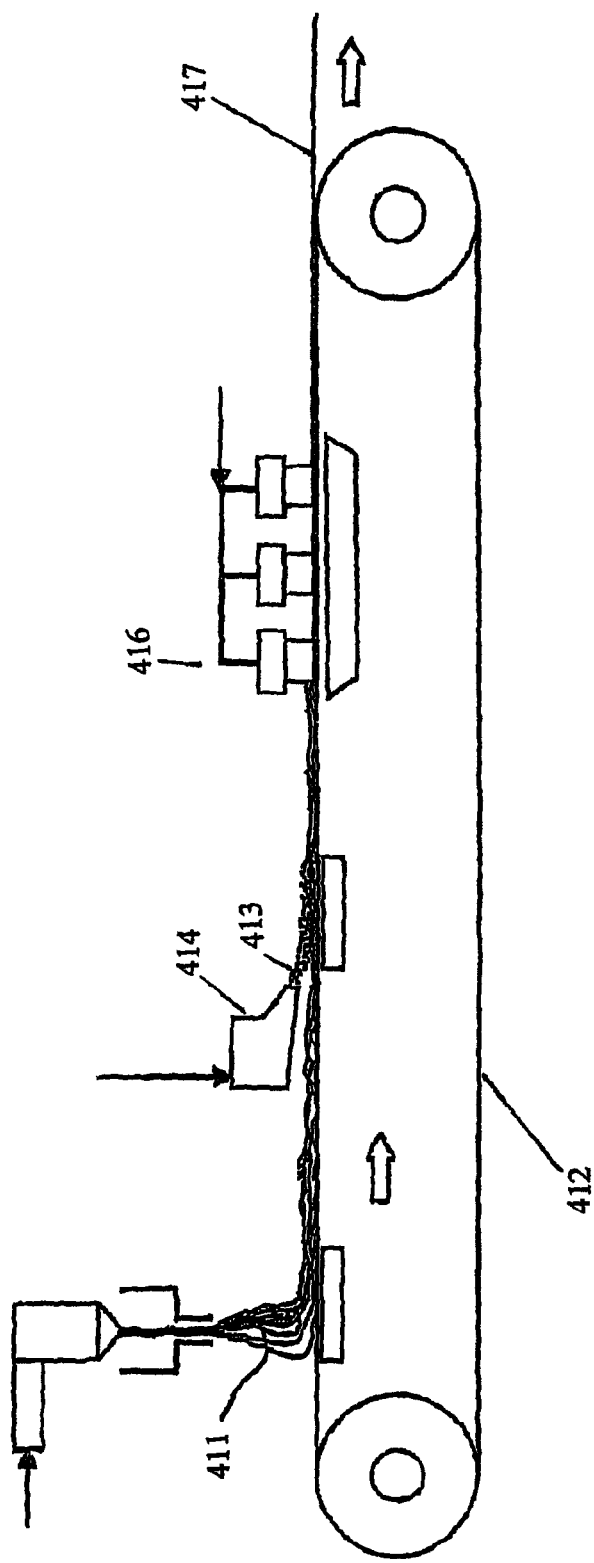
FIG. 4 shows schematically an embodiment of a process for producing a nonwoven material according to an embodiment of the invention.

Hereby follows the description of a method for producing the nonwoven material. FIG. 4 shows schematically an embodiment of a process for producing a nonwoven material according to the invention. The method of producing a nonwoven material, comprises forming a web of continuous filaments on a forming wire 412 and applying a wet- or foam formed fibre dispersion containing staple fibres on top of said continuous filaments, thus forming a fibrous web in containing the continuous filaments and the staple fibres and subsequently hydroentangling the fibrous web to form, a nonwoven material.

The embodiment shown in FIG. 4 starts with producing continuous filaments 411 in the form of spunlaid fibres by extruding a molten polymer, cool and stretch to an appropriate diameter.

According to the embodiment shown in FIG. 4, the spunlaid fibres 411 are laid down directly on a forming wire 412 where they are allowed to form a relatively loose, open web structure in which fibres are relatively free from each other. This is achieved either by making the distance between the spunlaying nozzle and the wire relatively large, so that the filaments are allowed to cool down before they land on the wire 412, at which their stickiness is reduced.

An aqueous or a foamed fibrous dispersion 413 from a headbox 414 is laid on top of the spunlaid filaments. In wet laying technique the fibres are dispersed in water, with optional additives, and the fibre dispersion is dewatered on a forming fabric to form a wet laid fibrous web. In the foam forming technique a fibrous web is formed from a dispersion of fibres in a foamed liquid containing water and a tensile. The foam forming technique is described in for example GB 1,329,409, U.S. Pat. No. 4,443,297, WO 96/02701 and EP-A-0 938 601. A foam-formed fibrous web has a very uniform fibre formation. For a more detailed description of the foam forming technique reference is made to the above mentioned documents.

The spunlaid filaments and the fibre dispersion of staple fibers may be formed on the same or on different wires. The web of spunlaid filaments laid on the wire 412 is substantially unbonded, which means that the web is very weak and has to be handled and transferred to the next forming station, the headbox 414, very gently.

According to one embodiment a relatively coarse forming wire 412 is used. This will aid in "binding" or "holding" the web of spunlaid filaments to the wire by bending, up and down and conforming to the topography of the wire and thus preventing it from moving when the wet- or foam formed fibre dispersion flushes down from the headbox 412 on top of the spunlaid web.

Fibre of many different kinds and in different mixing proportions can be used for making the wet laid or foam formed fibrous web. Varying fibre lengths can be used. However, it can be an advantage to use staple fibres having the length up to 20 mm. This is for some applications an advantage because the short fibres will more easily mix and integrate with the spunlaid filaments than longer fibres. There will also be more fibre ends sticking out from the material, which increases softness and textile feeling of the material. For short staple fibres both wet laying and foam forming techniques may be used.

In foam forming techniques, longer fibres, about 18-30 mm, can be used than what is possible with wetlaying techniques. Long fibres may in another aspect of the invention be an advantage, since they increase the strength of the hydroentangled material in dry as well as in wet condition.

The fibre dispersion laid on top of the spunlaid filaments can be dewatered by suction boxes (not shown) arranged under the wire 412. The wet- and foam formation benefits from an increased openness in the forming wire 412. The staple fibres are formed on top of the spunlaid web, which provides the necessary closeness and acts like an extra sieve for the formation of the staple fibres. Also, from this point of view, the choice of forming wire 412 may be done from the coarse end of the available spectrum.

The thus formed fibrous web comprising spunlaid filaments and staple fibres is quite stable by the presence of the staple fibres that will interlock the spunlaid fibres, which in their turn, reinforce the structure. The web is then hydroentangled in an entangling station 416 including several rows of nozzles, from which very fine water jets under high pressure are directed against the fibrous web. For a further description of the hydroentangling technique or, as it is also called, the spunlace technique, reference is made to e.g. CA patent 841,938.

Alternatively, the fibrous web can before hydroentangling be transferred to a special entangling wire, which optionally may be patterned in order to form a patterned nonwoven fabric. In this case the web can also, prior to the transfer, be hydroentangled by a first entangling station with one or more rows of nozzles in order to consolidate the web. However such a preentangling will nest the material to the wire, which will require a successively increasing draw in the transfer to the entangling wire. In an alternative embodiment the fibrous web is formed and hydroentangled on the same wire 412.

The hydroentangling may in a known manner be made from both sides of the fibrous material (not shown) at which a more homogeneous equilateral material is obtained.

The forming wire 412 and/or the entangling wire 416 may of course be substituted for another appropriate forming and entangling member respectively, such as an apertured belt, an apertured drum etc. The formation of the whole composite material is completed on the same wire, which can be relatively coarse.

After the hydroentangling the material 417 can be dried and wound up. The material can be then converted in a known manner to a suitable format and packed. Since it can be preferred to have closed loops of process water as far as this is possible, the water that has been dewatered at the forming and hydroentangling steps can be preferably recirculated.

The staple fibre layer may also be carded as mentioned above. However, a carding step cannot be made when the fibres have been laid onto the filament layer. The carding step has to be done before the staple fibre layer is put onto the filament layer.

The nonwoven material is thus a hydroentangled nonwoven material, which will achieve a nonwoven material which is mechanically bonded. This nonwoven material has a very good textile comfort and the same time has a very good inlet function.

The invention claimed is:

1. A nonwoven material comprising
    at least two layers integrated into each other, for use as a body facing sheet in an absorbent article,
    wherein the first layer comprises spunlaid filaments and the second layer comprises staple fibres,
    wherein the staple fibres have a thickness ≤0.7 dtex and the filaments are continuous and have a thickness ≥2.5 dtex,
    the staple fibres constitute 10-40% by weight of the material and the filaments constitute 60-90% by weight of the material, and
    the non-woven material has a surface weight of 20-50 g/m².

2. The nonwoven material according to claim 1, wherein the staple fibres have a thickness ≤0.5 dtex.

3. The nonwoven material according to claim 1, wherein the staple fibres have a length of 6 to 40 mm.

4. The nonwoven material according to claim 3, wherein the staple fibres have length of 6 to 20 mm.

5. The nonwoven material according to claim 1, wherein the filaments have a thickness ≥3 dtex.

6. The nonwoven material according to claim 1, wherein the filaments are man-made filaments.

7. The nonwoven material according to claim 1, wherein the filaments are polyethylene filaments, polypropylene filaments, polyamide filaments, polyester filaments, polyacrylic filaments or polylactide filaments.

8. The nonwoven material according to claim 1, wherein the staple fibres are man-made fibres or silk fibres.

9. The nonwoven material according to claim 1, wherein the staple fibres are polyethylene fibres, polypropylene fibres, polyamide fibres, polyester fibres, polyacrylic fibres, polylactide fibres, viscose fibres, lyocell fibres or silk fibres.

10. The nonwoven material according claim 1, wherein the layers are hydroentangled together.

11. An absorbent article comprising at least two layers integrated into each other, for use as a body facing sheet in an absorbent article,
   wherein the first layer comprises spunlaid filaments and the second layer comprises staple fibres,
   the staple fibres have a thickness ≤0.7 dtex and the filaments are continuous and have a thickness ≥2.5 dtex,
   the staple fibres constitute 10-40% by weight of the material and the filaments constitute 60-90% by weight of the material, and
   the non-woven material has a surface weight of 20-50 g/m$^2$.

12. The absorbent article according to claim 11, wherein the body facing sheet is a top sheet.

13. The absorbent article according to claim 11, wherein the second layer is directed against a body of a user during use.

* * * * *